United States Patent [19]

Polefka et al.

[11] Patent Number: 5,610,194
[45] Date of Patent: Mar. 11, 1997

[54] INSECT REPELLING COMPOSITIONS COMPRISING MIXTURES OF AN N-ALKYL NEOALKANAMIDE AND DEET

[75] Inventors: Thomas G. Polefka, Somerset; Pallassana Ramachandran, Robbinsville; Robert J. Steltenkamp, Somerset; Thomas F. Connors, Piscataway; Kevin M. Kinscherf, Freehold, all of N.J.

[73] Assignee: Colgate-Palmolive Company, New York, N.Y.

[21] Appl. No.: 662,745

[22] Filed: Jun. 10, 1996

[51] Int. Cl.⁶ ..................................... A01N 37/18
[52] U.S. Cl. ................ 514/617; 514/625; 514/627; 514/628; 514/629; 514/919; 510/383; 510/131; 510/214; 510/319
[58] Field of Search ..................... 514/617, 625, 514/626, 627, 628, 629, 919; 252/106, 107

[56] References Cited

U.S. PATENT DOCUMENTS

| | | | |
|---|---|---|---|
| 5,391,578 | 2/1995 | Steltenkamp | 514/625 |
| 5,434,189 | 7/1995 | Steltenkamp | 514/625 |
| 5,434,190 | 7/1995 | Steltenkamp | 514/629 |

*Primary Examiner*—John Pak
*Attorney, Agent, or Firm*—Bernard Lieberman; James M. Serafino

[57] ABSTRACT

Insect repellent compositions are provided comprising mixtures of:

(a) from about 5 to about 95%, by weight, of an N-alkyl neoalkanamide having the formula:

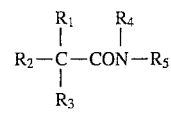

wherein $R_1$, $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

Preferred repellent composition comprise mixtures of N-methyl neodecanamide (MNDA) and DEET which provide synergistic repellency effects against a variety of insects including cockroaches, silverfish, mosquitoes, flies and ants. The repellent compositions may be applied directly to surfaces to be treated or they may be incorporated in detergent compositions such as laundry detergents, floor and wall cleaners, rug cleaners and shampoos, hair shampoos and liquid and bar soaps.

17 Claims, No Drawings

INSECT REPELLING COMPOSITIONS COMPRISING MIXTURES OF AN N-ALKYL NEOALKANAMIDE AND DEET

BACKGROUND OF THE INVENTION

This invention relates to insect repelling compositions having long lasting effectiveness against a wide variety of insects. More particularly, this invention relates to insect repelling compositions containing synergistic mixtures of an N-alkyl neoalkanamide, such as, N-methyl neodecanamide (MNDA) and N,N-diethylmeta-toluamide (DEET).

Many types of insects common in households, such as house cockroaches, are classified as pests, and much effort has been made to eradicate or at least to control them. Mosquito repellents have long been marketed and various chemicals that are effective in repelling roaches have been discovered. Typically, these chemicals and repellents are used in the household by applying or spraying them to surfaces of walls, floors, cabinets, drawers, packages, containers, rugs, upholstery and carpeting, and in potential nesting places for insects, such as inside walls and between floors.

N-lower alkyl neoalkanamides are well known and described in the patent literature as particularly efficacious insect repellent compounds. Indeed, the efficacy of these neoalkanamides, and in particular, N-methyl neodecanamide (MNDA) is underscored by the fact that they manifest longer lasting repellency effects than the well-known commercial all-purpose repellent N,N-diethyl-meta-toluamide known commonly as "DEET". Included among the patents which describe these N-alkyl neoalkanamide insect repellents as well as processes for their manufacture and use are, U.S. Pat. Nos. 5,006,562; 5,015,665; 5,143,900; 5,182,304; 5,182,305; 5,258,408; 5,391,578; and 5,434,189; the disclosures of which are incorporated herein by reference.

Notwithstanding the general effectiveness of N-alkyl neoalkanamides as insect repellents and the commercial success of DEET as the active component in numerous insect repellent sprays, efforts continue to be made to provide insect repellents which are capable of providing even greater repellency effects and for longer periods of time than those presently available, and even to be used in lesser quantity giving the same effect.

SUMMARY OF THE INVENTION

The present invention provides an insect repellent composition comprising a mixture of:

(a) from about 5 to about 95%, by weight, of an N-alkyl neoalkanamide having the formula:

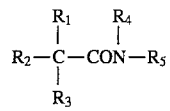

wherein $R_1$ $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

The present invention is predicated on the discovery that insect repellent compositions comprised of a blend of (a) an N-alkyl neoalkanamide, such as N-alkyl neotridecanamide (where the sums of the carbon atoms in $R_1$, $R_2$ and $R_3$ is 11), and preferably methyl neodecanamide (MNDA) (where $R_5$ is methyl, $R_4$ is hydrogen and the sum of the carbon atoms in $R_1$, $R_2$ and $R_3$ is 8, the resulting neoalkanoyl moiety being neodecanoyl), and (b) DEET, in accordance with the present invention manifest a synergistic repellency with regard to a variety of household pests and insects. Thus, the synergistic mixture of DEET and N-alkyl neoalkanamide is capable of providing longer-lasting repelling effects with regard to a particular insect than the additive repellency effects provided by comparative compositions which contain (i) the same amount of the N-alkyl neoalkanamide as in the mixture but in the absence of DEET, and (ii) the same amount of DEET as in the mixture but in the absence of the N-alkyl neoalkanamide, respectively.

Other useful N-alkyl neoalkanamides are N,N-dimethyl neodecanamide and N,N-diethyl neodecanamide. These are tertiary neoalkanamides where the sum of the carbon atoms in $R_1$, $R_2$, $R_3$ is 8, $R_4$ and $R_5$ are the same and are either methyl, ethyl, or propyl, respectively.

Useful mixtures of the N-alkyl neoalkanamide and DEET for purposes of the invention are generally in a weight ratio of neoalkanamide to DEET of from about 95:5 to as low as 40:60. When the neoalkanamide is MNDA, preferred mixtures are within a weight ratio of from about 90:10 to about 60:40, and most preferably from about 90:10 to about 80:20.

In accordance with the process aspect of the invention, there is provided a process for repelling insects from an area, location or item which comprises applying to or near such area, location or item an insect repelling quantity of an insect repellent composition comprising a mixture of:

(a) from about 5 to about 95%, by weight, of an N-alkyl neoalkanamide having the formula:

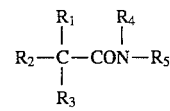

wherein $R_1$ $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

The preferred N-alkyl neoalkanamide in the defined repellent composition for use in accordance with the process is MNDA.

There is also provided herein an aqueous liquid detergent composition for cleaning a hard surface and for repelling insects therefrom comprising (i) a detersive proportion of a surface active detergent compound selected from the group consisting of anionic, nonionic, cationic and amphoteric detergent compounds and mixtures thereof; (ii) at least about 50%, by weight, water; and (iii) an effective amount of an insect repellent composition which is sufficient to repel insects from such hard surface after application of the liquid detergent composition thereto, said repellent composition comprising a mixture of:

(a) from about 5 to about 95%, by weight, of an N-alkyl neoalkanamide having the formula:

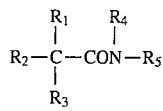

wherein $R_1$, $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

To make the neoalkanamides of this invention neoalkanoyl chloride reactant is slowly reacted with the appropriate primary amine, in ethyl ether, after which reaction the reaction mixture is washed with distilled water, dilute hydrochloric acid solution, dilute sodium hydroxide solution, and more distilled water, until it is neutral to pH paper. The ether is then removed by means of a steam bath, followed by employment of a vacuum evaporator. The reaction product obtained is water white to light amber in color and is essentially pure. In an alternative method, the neoalkanoic acid may be reacted directly with the lower alkylamine.

Neoalkanoic acids, such as neodecanoic acid, neotridecanoic acid, neoheptanoic acid and neopentanoic acid, are available from Exxon Chemical Company, which synthesizes them by reacting a suitable branched alkene and carbon monoxide under higher pressure at elevated temperature in the presence of aqueous acidic catalyst (Koch reaction). The general mechanism involved includes generation of carbonium ion, followed by complexation with carbon monoxide and the catalyst to form a "complex", which is subsequently hydrolyzed to generate free acid. The formula of the free acid is

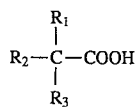

and the neoalkanoyl moiety is

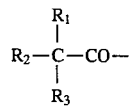

In neodecanoic acid, for example, the total number of carbon atoms in $R_1$, $R_2$ and $R_3$ is 8, 31% of the neodecanoic acid is of a structure wherein $R_1$ and $R_3$ are both methyl and $R_2$ is hexyl, 67% is of a formula wherein $R_1$ is methyl, $R_3$ is alkyl of a carbon atoms content greater than that of methyl and less than that of $R_2$ and $R_2$ is of a carbon atoms content less than that of hexyl and greater than that of $R_3$; and 2% is of the formula wherein $R_1$ and $R_3$ are both of a carbon atoms content greater than that of methyl and less than that of $R_2$ and $R_2$ is of a carbon atoms content less than that of hexyl and greater than those of $R_1$ and $R_3$. Among other neoalkanoic acids that are available and useful to make the present amides may be mentioned others in the 7 to 16 carbon atoms content range, such as neoheptanoic, neononanoic, neodecanoic, neododecanoic, neotridecanoic and neotetradecanoic acids. In the various neoalkanoic acids mentioned, when $R_2$ is alkyl of five or more carbon atoms, such alkyl is branched. The acyl chloride starting materials for the reactions to produce the invented N-lower alkyl neoalkanamides may be made from the neoalkanoic acids and suitable chlorinating agents, such as phosphorus trichloride (although sometimes thionyl chloride may be found preferable) and are available from the PPG Industries, Inc. and from BASF Corporation.

Although it is possible for the insect repellents of this invention to be incorporated in various materials when such materials are being manufactured, as by being mixed in with pulp for making paper, rubber and synthetic organic polymeric plastic batches, and chips for the manufacture of pressed boards, and while the invented insect repellents may also be injected or otherwise inserted into the bodies of items to be made insect repellent, usually the insect repellents will be applied to surfaces of areas, structures or items to be made insect repellent, either by direct application of the insect repelling composition, in liquid solution or dispersion, or dispersed in a powdered carrier, or in a detergent composition, such as a laundry detergent, floor or wall cleaner, upholstery or rug shampoo, hair shampoo, liquid soap, bar soap, or in any other appropriate composition in which it may be usefully incorporated. Among such other appropriate compositions may be mentioned antibacterial washes or dips for humans, pets and farm animals, furniture polishes and finishes, floor waxes and finishes, ointments, lotions, salves and topical medicaments, after shaves, insecticides, fungicides, bactericides, plant fertilizers, mulches and plant potting preparations, to name only a few. In the majority of instances, the invented compositions will be applied directly or indirectly by external application to surfaces to be treated, and afterward such application will be made on a continuing basis to maintain a satisfactory degree of insect repellency. Thus, the insect repellent compositions containing a mixture of DEET and an N-alkyl neoalkanamide, such as N-methyl neodecanamide and/or N-methyl neotridecanamide, may be painted onto a surface to be treated or may be applied to such surface by washing it with a detergent composition containing the active insect repellent. The invented compounds are in liquid state or pasty condition at normal ambient temperatures and are water insoluble, so they tend to be satisfactorily substantive to surfaces from detergent compositions and from other preparations, even when such compositions are rinsed off, and normally, after either direct or indirect application to such surfaces, a sufficient amount of the repellent compositions of the invention will remain to be effectively insect repelling.

It is generally considered that insect repellent effects are obtainable at surface concentrations of the active ingredients in the range of 0.002 to 100 g./sq. m. For economic reasons and for effectiveness against such insects there will normally be applied a concentration from 0.01 to 5 g./sq. m., preferably 0.1 to 2 g./sq. m., e.g., 1 g./sq. m., when roach repellency is desired. Higher application rates, such as 10 to 100 g./sq. m., will often be used against mosquitoes.

Because the present insect repellent compositions are volatile their presence can be detected in the air near a surface to which they have been applied. Therefore, not only are the surfaces repellent to insects, which will avoid having their body parts contact such surfaces, but the vapors from the repellent compositions will tend to repel insects from the surrounding space. Thus, the application of the volatile repellent to walls of a china closet can repel roaches from the closet interior, thereby preventing them from contacting, soiling and contaminating contained dishes, utensils and silverware. Similarly, coating of pantry surfaces, interior and/or exterior, with a furniture polish containing an invented volatile repellent, or use of shelf paper containing a repellent neoalkanamide can discourage roaches from entering the pantry and contaminating foods contained therein. Also, washing the skin and hair or clothing with detergent compositions containing the invented repellents may prevent insects from lighting and stinging or biting the wearer. Shampooing of a rug with a rug shampoo or carpet cleaner containing the invented repellent will discourage insects from entering the room and from nesting and laying their eggs in or under the rug. Washing of floors and walls with insect repellent detergent compositions formulated for such purpose will deposit thereon a substantive coating of the invented insect repellent composition and will discourage insects from contacting the floor and wall surfaces and from entering the treated rooms. It is an important feature of the present compositions that although they are sufficiently volatile to be effective, their repellent properties are persistent, often lasting as long as three weeks or more (even longer if incorporated interiorly in a product). The invented repellents may be formulated for certain applications with insecticides, such as by being sprayed onto the surfaces of insecticidal powders, e.g., boric acid powder, which is effective against roaches. But the preferred practice is to formulate and use the insect repellent compositions of the invention in the absence of any insecticide thereby avoiding the disadvantage normally associated with the use of insecticides, namely, toxicity, and the ability of insects to develop resistance thereto of an unlikely occurrence with repellents.

It is apparent from the foregoing brief description that the invented insect repellents can be used in many compositions and can be applied in diverse ways. However, among the most useful products which can incorporate the invented repellents are detergent compositions, from which the repellents are surprisingly substantive to the surfaces of washed items. Such detergent compositions operate in several ways to counter insect contamination of the washed item. They remove any earlier contamination, remove stains and soils, on which the insects might feed, and which could attract them, and leave behind the insect repelling mixture of neoalkanamide and DEET.

The detergent compositions contain a detersive proportion of one or more surface active detergent compounds from among anionic, nonionic, cationic and amphoteric detergents, which generally will be in the range of from about 1 to about 30%, by weight, of the composition, preferably from about 2 to about 20%, by weight. The detergent is preferably a synthetic organic detergent of the anionic or nonionic type and often a combination of anionic and nonionic detergents will be most preferred. Descriptions of many such detergents are found in the text *Surface Active Agents and Detergents,* Vol, II, pages 25–138, by Schwartz, Perry and Berch, published in 1958 by Interscience Publishers, Inc. Such compounds are also described in a 1973 publication by John W. McCutcheon, entitled *Detergents and Emulsifiers.* Both such publications are incorporated herein by reference.

The anionic detergents employed will normally be salts of alkali metals, such as sodium or potassium or ammonium or lower alkanolammonium salts, e.g., triethanolamine salts. The anionic detergent may be a sulfate, sulfonate, phosphate or phosphonate or salt of other suitable acid but usually will be a sulfate or sulfonate. The anionic detergents include a lipophilic group, which will normally have from 10 to 18 carbon atoms, preferably in linear higher alkyl arrangement, but other lipophilic groups may be present instead, preferably including 12 to 16 carbon atoms, such as branched chain alkyl benzene. Examples of suitable anionic detergents include higher fatty alcohol sulfonates, such as sodium tridecylbenzene sulfonate; sodium linear alkyl benzene sulfonates, e.g., sodium linear dodecylbenzene sulfonate; olefin sulfonates; and paraffin sulfonates. The anionic detergents are preferably sodium salts but potassium, ammonium and triethanolammonium salts are often more desirable for some liquid compositions.

The suitable nonionic detergents will normally be condensation products of lipophilic compounds or moieties and lower alkylene oxides or polyalkoxy moieties. Highly preferable lipophiles are higher fatty alcohols of 10 to 18 carbon atoms but alkyl phenols, such as octyl and nonyl phenols, may also be used. The alkylene oxide of preference is ethylene oxide and normally from 3 to 30 moles of ethylene oxide will be present per mole of lipophile. Preferably such ethoxylate content will be 3 to 10 moles per mole of higher fatty alcohol and more preferably it will be 6 to 7 moles, e.g., 6.5 or 7 moles per mole of higher fatty alcohol (and per mole of nonionic detergent). Both broad ranges ethoxylates and narrow range ethoxylate (BRE's and NRE's) may be employed, with the difference between them being in the "spread" of number of ethoxylate groups present, which average within the ranges given. For example, NRE's which average 5 to 10 EtO groups per mole in the nonionic detergent will have at least 70% of the EtO content in polyethoxy groups of 4 to 12 moles of EtO and will preferably have over 85% of the EtO content in such range. BRE nonionic detergents have a broader range of ethoxy contents than NRE's, often with a spread from 1 to 15 moles of EtO when the EtO chain is in the 5 to 10 EtO range (average). Examples of the BRE nonionic detergents include those sold by Shell Chemical Company under the trademark Neodol$^R$, including Neodol 25-7, Neodol 23-6.5 and Neodol 25-3. Supplies of NRE nonionic detergents have been obtained from Shell Development Company, which identifies such materials as 23-7P and 23-7Z.

Cationic surface active compounds may also be employed. They comprise surface active detergent compounds which contain an organic hydrophobic group which forms part of a cation when the compound is dissolved in water, and an anionic counter ion. Typical cationic detergents are amine and quaternary ammonium compounds.

The quaternary ammonium compounds useful herein are known materials and are of the high-softening type. Included are the $N_1N$-di-(higher) $C_{14}$–$C_{24}$, $N_1N$-di(lower) $C_1$–$C_4$ alkyl quaternary ammonium salts with water solubilizing anions such as halide, e.g. chloride, bromide and iodide; sulfate, methosulfate and the like and the heterocyclic amides such as imidazolinium.

For convenience, the aliphatic quaternary ammonium salts may be structurally defined as follows:

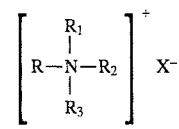

wherein R and $R_1$ represent alkyl of 14 to 24 and preferably 14 to 22 carbon atoms; $R_2$ and $R_3$ represent lower alkyl of 1 to 4 and preferably 1 to 3 carbon atoms, X-represents an anion capable of imparting water solubility or dispersibility including the aforementioned chloride, bromide, iodide, sulfate and methosulfate. Particularly preferred species of aliphatic quats include:
distearyl dimethylammonium chloride
di-hydrogenated tallow dimethyl ammonium chloride
di tallow dimethyl ammonium chloride
distearyl dimethyl ammonium methyl sulfate
di-hydrogenated tallow dimethyl ammonium methyl sulfate.

Amphoteric detergents are also suitable for the invention. This class of detergents is well known in the art and many operable detergents are disclosed by Schwartz, Perry and Berch in "Surface Active Agents and Detergents", Vol. II, Interscience Publishers, Inc., New York (1958) in Chapter 4 thereof. Examples of suitable amphoteric detergents include: alkyl betaiminodipropionates, $RN(C_2H_4COOM)_2$; and alkyl beta-amino propionates, $RN(H)C_2H_4COOM$.

Builders may be present in the liquid detergent composition in an amount of from about 1 to 20% to improve the detergency of the synthetic organic detergents. Such builders may be inorganic or organic, water soluble or water insoluble. Included among such builders are polyphosphates, e.g., sodium tripolyphosphate; carbonates, e.g., sodium carbonate; bicarbonates, e.g., sodium bicarbonate; borates, e.g., borax; and silicates, e.g., sodium silicate; water insoluble inorganic builders, including zeolites, e.g., hydrated Zeolite 4A; and water soluble organic builders, including citrates, gluconates, NTA, and polyacetal carboxylates.

Various adjuvants may be present in the detergent compositions such as fluorescent brighteners, antistatic agents, antibacterial agents, fungicides, foaming agents, anti-foams, flow promoters, suspending agents, antioxidants, anti-gelling agents, soil release promoting agents, and enzymes.

The liquid detergent compositions of the invention will generally comprise from about 2 to 20% of surface active detergent compounds which are preferably anionic and/or nonionic, from about 1 to 20%, by weight, of builder salts for such detergents and from about 0.2 to 20%, preferably 0.5 to 10%, by weight, of the insect repellent material, the balance being predominantly water, adjuvants and optionally an emulsifying agent, or hydrotrope such as sodium toluene sulfonate or a solvent suitable for the insect repellent material such as isopropyl alcohol or acetone. To facilitate the incorporation of a fragrance or perfume into the aqueous liquid detergent composition, it is often advantageous to formulate the liquid detergent composition in microemulsion form with water as the continuous phase and oil or hydrocarbon as the dispersed phase.

EXAMPLE 1

The repellency bioassays described below were conducted with various mixtures of MNDA and DEET, repellent compositions in accordance with the invention, to determine their repellency with regard to the following insects:

| Species | Common Name |
|---|---|
| *Supella longipalpa* | Brown-Banded Roach |
| *Periplanta americana* | American Roach or Palmetto Bug |
| *Ctenolepisma saccharina* | Silverfish |
| *Camponotus compressus* | Carpenter Ant |
| *Monomorium gracillimum* | Black Ant |
| *Anopheles stephensi* | Mosquito |
| *Culex quinquefasciatus* | Mosquito |
| *Aedes aegypti* | Mosquito |
| *Musca domestica* | Fly |

Insect Collection & Maintenance

Collections of male and female cockroaches from storehouses in the area of Madras, India were brought to the laboratory and maintained in plastic cages (50×25 cm).

Male and female silverfish were collected from storehouses in the area of Madras, India. They were maintained in plastic tubes (50×25 cm). Filter paper strips were provided as a food source and for shelter. Ventilation was provided by small holes in the plastic tubes. Water was provided.

Colonies of *Camponotus compresses* and *Monomorium gracillimum* were brought to the laboratory along with some of the original nest materials and populations of up to 20,000 were maintained in plastic tubs (50×25 cm). Ants were collected from their natural habitat in the area of Madras, India. The queen, males and workers were transferred to the plastic cage. The ants were allowed to settle down by making tunnels and galleries. The nests were moistened by a few drops of water along the sides of the jars to prevent the soil debris from getting dry. Thereafter, very few ants could be spotted moving around indicating the establishment of the colony inside. Food and water were provided.

Unifected, laboratory strains of *Anopheles stephensi, Culex quinquefasciatus,* and *Aedes aegypti* mosquitoes were grown separately in trays of fresh water and fed a mixture of yeast and dog biscuit. The common housefly, *Musca domestica*, was grown on a mixture of bananas and yeast.

Repellency Bioassays—Cockroaches

A modification of the method of Goodhue and Tissol described in *J. Econ. Entomol.* (1952) at pp. 45, 133–134, "Determining the Repellent Action of Chemicals to the American Cockroach" was used to evaluate the repellency of MNDA: DEET mixtures. With few exceptions, this is similar to the method described in *J. Med. Entomol.* (1992) 29, pp. 141-149. Each test consisted of replicated two-choice assays in which cockroaches were offered treated versus untreated shelters over a period of days. Repellency was quantified based on the relative distribution of resting cockroaches during the light phase of their light-dark cycle. Cockroaches prefer the dark and individuals are almost always found in one of the two shelters. An effective repellent treatment causes roaches to shelter in the control cup.

The experimental set up consisted of a plastic cage containing the acclimatized test insects into which two paper Dixie cups were placed and maintained in inverted positions. Openings at the base facilitated the free movement of the insects. One cup was treated with 2 ml of an 2-propanol solution of MNDA, DEET, or a mixture of the two compounds. The other cup was the control and was treated only with 2-propanol. Five hours after treatment both cups had dried and were placed inside the plastic cage and 10 Supella or 50 Periplanta were introduced into the center of the cage. Food was placed within the cups. Water was provided. Five setups were maintained as replicates.

The number of insects resting inside each shelter was recorded daily during the middle of the 12 hr light portion of the photocycle. After each reading, all cockroaches were removed from each shelter and the positions of the shelters were reversed. Assays were terminated after 30 days or when equal numbers of insects were found in treated and control shelters.

Repellency Bioassay—Silverfish

The repellency bioassay was the same as for cockroaches noted above.

Repellency Bioassay—Ant (*Camponotus compressus*)

The experimental set up consisted of two transparent plastic jars (control and experimental, both 24×12 cm) connected to the central ant culture chamber using PVC tubes (15×5 cm). The sides of the culture chamber were provided with small openings for ventilation. Long paper strips were placed in each connecting tube to facilitate movement of ant with in the tubes. This set-up was maintained until the ants started moving across the tubes. Exactly a week before the start of experiments, vinyl tiles were placed at the bottom of each container. Biscuits were placed on the tiles so that ants would begin foraging. Subsequently, the experimental tile was treated with 2 mL of an 2-propanol solution of MNDA, DEET or a mixture of the two compounds. The other tile was the control and was treated only with 2-propanol. The number of ants found on the treated and control tiles were recorded until equal numbers of ants were recorded. This experiment was replicated five times.

(*Monomorium gracillimum*)

A different bioassay system was used for these smaller ants. The experimental set-up was a MAC (Multi Axis Chamber) which consisted of a transparent plastic jar (24× 12 cm) which served as the colony chamber and was placed at the center. Connected to it by PVC tubes (2×10 cm) were six small plastic jars, of which five small containers (10×7 cm) served as the experimental chambers and a larger container (15×10 cm) served as a control chamber. Paper strips were provided to facilitate the easy mobility of ants over the smooth interior of the chamber. Prior to the start of the bioassay, the ant colony was allowed to establish and settle inside the large central colony chamber. Subsequently, tiles treated with 2 ml of a 2-propanol solution of either MNDA, DEET or a mixture of the two compounds were placed in the small experimental containers along with food. The number of ants found on the treated and control tiles were recorded until 25 equal numbers of ants were recorded. This experiment was replicated five times.

Repellency Bioassays—Mosquitoes

The tendency of mosquitoes to rest upon cloth surfaces when not feeding was used as a measure of insect repellency. This approach was chosen to obviate the need of exposing animals or human subjects to insect bites. Lab-bred mosquito pupae were transferred to test chambers prepared from cardboard boxes (45cm×30cm×30 cm). To permit observation and allow for ventilation, the top of box was removed and covered with mosquito netting. Access to the interior of the chamber was provided by two holes (10 cm diameter) cut into the front face of the box and covered with mosquito netting. The inner surface of the chambers was lined with muslin cloth which served as the resting surface for the mosquitos.

To measure the repellency of the test compounds and mixture thereof, two opposing walls of the experimental chambers were treated with isopropyl alcohol (vehicle) and the remaining two walls were treated with 1% MNDA or DEET either alone or as a mixture in isopropyl alcohol. The test compounds were applied uniformly over the cardboard surface to a final coverage of 2.1 µg/cm$^2$. After drying for four hours, 100 mosquitoes were introduced into the test chamber. An observer noted at appropriate times the location of the resting mosquitoes. Repellent efficacy was defined as the length of time before mosquitoes began resting on the repellent treated surface (i.e., days of 100% repellency). All data reported in Table 4 represents the means of ten experiments.

Repellency Bioassays—Flies

To measure the efficacy of the experimental compounds as fly repellents, vinyl floor tiles (25 cm$^2$) were treated uniformly with either 2 ml isopropyl alcohol or 2 ml repellent compound or mixtures of MNDA or DEET dissolved in isopropyl alcohol to yield a final concentration of 2%. The tiles were placed onto a glass plate located inside test chambers identical to those used to measure mosquito repellency. A food source in a small dish was placed on top of each tile. The experiment was initiated by the introducing 100 hundred flies into the test chamber. An observer noted at appropriate times the feeding location of the flies. Repellent efficacy was defined as the length of time the flies stayed away from the tile treated with the repellent compound(s).

Data Analysis

From daily recordings of the relative position of the insects, percent repellency was calculated as follows:

% Repellency=100 −[100 * ($N_t/[N_t+N_c]$)]

where $N_t$ is the number of insects on the treated surface and $N_c$ is the number on the untreated control surface. For example, if out of the 50 insects found on either the treated or control surface, 2 were observed on the treated surface, then $N_t$=2 and $N_t+N_c$=50. It follows that % Repellency=96.

To evaluate the repellency, the number of days of complete (100%) repellency was noted.

Preparation of Samples

MNDA and DEET are very miscible allowing mixtures to be readily prepared. For example, a 90 part MNDA: 10 part DEET mixture was prepared by thoroughly blending together 90.0 grams of MNDA and 10.0 grams DEET. The purity of each of the individual repellents was greater than 95%. Once the various mixtures were blended, they were dissolved in 2-propanol. The solution concentration (wt./vol.) used for each species was determined in initial screening tests. Concentrations did not exceed 5%.

Table 1 shows results of the five replicate bioassays for cockroaches as described above. The concentration of repellent was 1% for *S. longipalpa* and 5% for *P. americana*. As evidenced by the data, the repellency provided by a wide range of mixtures demonstrated synergistic effects, namely, it was longer-lasting than the cumulative repellency provided by the individual repellents, MNDA and DEET, acting alone. The mixture of 90 parts MNDA and 10 parts DEET was a particularly preferred ratio to repel these pests.

TABLE 1

Repellency against Cockroaches

| Parts MNDA:Parts DEET | Days of 100% Repellency | |
|---|---|---|
| | *S. longipalpa* | *P. americana* |
| 100:0 MNDA Alone | 10.5 | 6.8 |
| 90:10 | 30.8 | 9.4 |
| 80:20 | 26.2 | 9.2 |
| 60:40 | 17.0 | 7.0 |
| 40:60 | 10.0 | 4.8 |
| 20:80 | 8.2 | 4.6 |
| 10:90 | 6.6 | 3.4 |
| 0:100 DEET alone | 7.4 | — |

Table 2 shows results of the five replicate bioassays for silverfish as described above. The concentration of repellent was 2%. As evidenced by the data, the repellency provided by a wide range of mixtures demonstrated synergistic effects, namely, it was longer-lasting than the cumulative repellency provided by the individual repellents, MNDA and DEET, acting alone. The mixture of 90 parts MNDA and 10 parts DEET was a particularly preferred ratio to repel these pests.

TABLE 2

Repellency against Silverfish

| Parts MNDA:Parts DEET | Days of 100% Repellency |
| --- | --- |
| 100:0 MNDA alone | 7.4 |
| 90:10 | 28.2 |
| 80:20 | 26.8 |
| 60:40 | 22.4 |
| 40:60 | 21.2 |
| 20:80 | 16.8 |
| 10:90 | 15.8 |
| 0:100 DEET alone | 6.0 |

Table 3 shows results of the five replicate bioassays for ants as described above. The concentration of repellent was 5% for *C. compressus* and 2% for *M. gracillimum*. As evidenced by the data, the repellency provided by a wide range of mixtures demonstrated synergistic effects, namely, it was longer-lasting than the cumulative repellency provided by the individual repellents, MNDA and DEET, acting alone. The mixture of 90 parts MNDA and 10 parts DEET was a particularly preferred ratio to repel these pests.

TABLE 3

Repellency against Ants

| | Days of 100% Repellency | |
| --- | --- | --- |
| Parts MNDA:Parts DEET | *C. compressus* | *M. gracillimum* |
| 100:0 MNDA alone | 3.0 | 4.4 |
| 90:10 | 12.2 | 14.0 |
| 80:20 | 10.4 | 11.8 |
| 60:40 | 9.0 | 9.2 |
| 40:60 | 8.2 | 8.4 |
| 20:80 | 7.6 | 7.2 |
| 10:90 | 6.2 | 6.2 |
| 0:100 DEET alone | 2.4 | 2.4 |

Table 4 presents the results of ten replicate bioassays for three species of mosquitoes and one specie of fly. In the the mosquito experiment the insect repellent compound or mixture was employed at coverage rate equivalent to 2.1 μg/cm$^2$ whereas for the fly experiment the coverage rate was 7.0 μg/cm$^2$. With the possible exception of *Aedes aegypti*, the combination of MNDA: DEET provided longer insect repellency than either compound acting alone. Based on the data in the table the 75:25 mixture of MNDA: DEET is the preferred ratio of repellents for protecting against *Anolpheles, stephensi, Culex quinquefasciatus,* and *Musca domestica.*

TABLE 4

Repellency against Mosquitoes and Flies

| | Days of 100% Repellency | | | |
| --- | --- | --- | --- | --- |
| Parts MNDA: Parts DEET | *Anopheles stephensi* | *Culex quinquefasciatus* | *Aedes aegypti* | *Musca domestica* |
| 100:0 MNDA alone | 5.0 | 5.0 | 7.8 | 8.5 |
| 75:25 | 5.2 | 5.8 | 7.6 | 12.8 |
| 50:50 | 5.0 | 4.0 | 4.2 | 11.0 |
| 25:75 | 3.6 | 3.6 | 2.0 | 9.0 |
| 0:100 DEET alone | 3.0 | 4.0 | 5.8 | 5.6 |

EXAMPLE 2

The repellency effects of a liquid cleaning composition containing 2%, by weight, of an insect repellent composition in accordance with the invention (Formula A) was measured and compared to the repellency provided by a control cleaning composition containing 2%, by weight, of MNDA as the sole repellent (Control Formula). Both formulas are in the form of microemulsions.

The composition of each formula is indicated below, the compositions being nearly identical except for the particular repellent which was used.

| | Weight Percent | |
| --- | --- | --- |
| Component | Formula A | Control Formula |
| Deionized Water | 82.23 | 82.23 |
| $C_{14}$–$C_{17}$ Paraffin Sulfonate (60%) | 6.67 | 6.67 |
| $C_{13}$–$C_{15}$ Fatty Alcohol EP 7:1/ PO 4:1 | 3.00 | 3.00 |
| Magnesium Sulfate Heptahydrate | 1.00 | 1.00 |
| Coco Fatty Acid | 0.50 | 0.50 |
| Caustic Soda (38%) | 0.05 | 0.05 |
| Diethylene Glycol Monobutyl Ether | 3.50 | 3.50 |
| MNDA/DEET 90:10 | 2.00 | — |
| MNDA | — | 2.00 |
| Fragrance | 0.80 | 0.80 |
| Adjuvants | balance | balance |

Table 5 shows the results of five replicate bioassays, respectively, for cockroaches, silverfish and ants as described above, using Formula A and the Control Formula as the respective repellent compositions. Repellency bioassays were the same as described in Example 1 except vinyl tiles were treated and assembled into shelters in these experiments in place of the paper Dixie cups used in certain of the bioassays of the previous examples. This bioassay is also described in a paper to be published in *International Pest Control* in the March/April 1996 issue.

TABLE 5

Repellency Against Cockroaches, Silverfish, and Ants

| | Days of 100% Repellency | |
| --- | --- | --- |
| Insect Species | Formula A | Control Formula |
| Cockroaches | | |
| *S. longipalpa* | 31.2 | 9.0 |
| *P. americana* | 3.0 | 1.6 |
| Silverfish | | |
| *C. saccharina* | 31.4 | 8.8 |
| Ants | | |
| *C. compressus* | 2.4 | 1.0 |
| *M. gracillimum* | 14.4 | 5.0 |

As indicated by the data, the repellency provided by Formula A containing a repellent in accordance with the invention was markedly superior to the repellency provided by the Control Formula containing a repellent outside of the present invention.

We claim:

1. An insect repellent composition comprising a mixture of:

(a) from about 5 to about 95%, by weight, of an N-alkyl neoalkanamide having the formula:

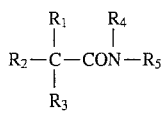

wherein $R_1$, $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

2. An insect repellent composition according to claim 1 wherein in the formula of (a) $R_5$ is methyl and the neoalkanoyl moiety of said N-alkyl neoalkanamide is neodecanoyl.

3. An insect repellent composition according to claim 2 wherein the respective amounts of N-methyl neodecanamide (MNDA) and DEET in said mixture are in a weight ratio of MNDA to DEET of from about 95:5 to about 60:40; and wherein the insect repellency effects provided by said mixture of MNDA and DEET is longer-lasting than the additive repellency effects provided by comparative compositions containing (i) the same amount of MNDA as in the mixture but in the absence of DEET, and (ii) the same amount of DEET as in the mixture but in the absence of MNDA.

4. An insect repellent composition according to claim 3 wherein said weight ratio of MNDA to DEET is from about 90:10 to about 80:20.

5. A process for repelling insects from an area, location or item which comprises applying to or near said area, location or item an insect repelling quantity of an insect repellent composition comprising a mixture of:

(a) from about 5 to about 95%, by weight, of an N-alkyl neoalkanamide having the formula:

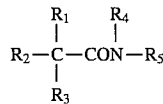

wherein $R_1$, $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

6. A process according to claim 5 wherein in the formula of (a) $R_5$ is methyl and the neoalkanoyl moiety of said N-alkyl neoalkanamide is neodecanoyl.

7. A process according to claim 6 wherein the weight ratio of MNDA to DEET in the mixture is from about 95:5 to about 60:40; and wherein the insect repellency effects provided by said mixture of MNDA and DEET is longer-lasting than the additive repellency effects provided by comparative compositions containing (i) the same amount of MNDA as in the mixture but in the absence of DEET, and (ii) the same amount of DEET as in the mixture but in the absence of MNDA.

8. A process according to claim 7 wherein said weight ratio of MNDA to DEET is from about 90:10 to about 80:20.

9. An aqueous liquid detergent composition for cleaning a hard surface and for repelling insects therefrom comprising (i) a detersive proportion of a surface active detergent compound selected from the group consisting of anionic, nonionic, cationic and amphoteric detergent compounds and mixtures thereof; (ii) at least about 50%, by weight, water; and (iii) an effective amount of an insect repellent composition which is sufficient to repel insects from said hard surface after application of the liquid detergent composition thereto, said repellent composition comprising a mixture of:

(a) from about 5 to about 95%, by weight, of an N-alkyl neoalkanamide having the formula:

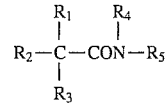

wherein $R_1$, $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

10. A liquid detergent composition as in claim 9 comprising from about 2 to about 20%, by weight, of said surface active detergent compounds, from about 1 to 20%, by weight of a builder salt, and from about 0.2 to about 20%, by weight, of said insect repellent composition.

11. A liquid detergent composition as in claim 9 wherein in the formula of (a), $R_5$ is methyl and the neoalkanoyl moiety of said N-alkyl neoalkanamide is neodecanoyl.

12. A liquid detergent composition as in claim 11 wherein the respective amounts of N-methyl neodecanamide (MNDA) and DEET in said mixture are in a weight ratio of MNDA to DEET of from about 95:5 to about 60:40; and wherein the insect repellency effects provided by said mixture of MNDA and DEET is longer-lasting than the additive repellency effects provided by comparative compositions containing (i) the same amount of MNDA as in the mixture but in the absence of DEET, and (ii) the same amount of DEET as in the mixture but in the absence of MNDA.

13. A liquid detergent composition as in claim 12 wherein the weight ratio of MNDA to DEET is from about 90:10 to about 80:20.

14. A process for cleaning a hard surface and for repelling insects therefrom comprising applying to said hard surface a liquid detergent composition comprising (i) a detersive proportion of a surface active detergent compound selected from the group consisting of anionic, nonionic, cationic and amphoteric detergent compounds; (ii) at least about 50%, by weight, water; and (iii) an effective amount of an insect repellent composition which is sufficient to repel insects from said hard surface after application of the liquid detergent composition thereto, said insect repellent composition comprising a mixture of:

(a) from about 5 to about 95%, by weight, of an N-alkyl neoalkanamide having the formula:

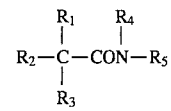

wherein $R_1$, $R_2$, and $R_3$ are alkyl groups and the sum of the carbon atoms therein is from 6 to 12, and wherein $R_4$ is either a hydrogen atom or an alkyl group having one to two carbon atoms, and wherein $R_5$ is methyl, ethyl, or propyl; and (b) from about 5 to about 95%, by weight, of N,N-diethyl-meta-toluamide (DEET).

15. A process according to claim 14 wherein in the formula of (a) $R_5$ is methyl and the neoalkanoyl moiety of said N-alkyl neoalkanamide is neodecanoyl.

16. A process according to claim 15 wherein the respective amounts of N-methyl neodecanamide (MNDA) and DEET in said mixture are in a weight ratio of MNDA to DEET of from about 95:5 to about 60:40; and wherein the insect repellency effects provided by said mixture of MNDA and DEET is longer-lasting than the additive repellency effects provided by comparative compositions containing (i) the same amount of MNDA as in the mixture but in the absence of DEET, and (ii) the same amount of DEET as in the mixture but in the absence of MNDA.

17. A process according to claim 16 wherein the weight ratio of MNDA to DEET is about 90:10 to about 80:20.

* * * * *